United States Patent [19]

Shell

[11] 4,115,544

[45] Sep. 19, 1978

[54] OCULAR SYSTEM MADE OF BIOERODIBLE ESTERS HAVING LINEAR ETHER

[75] Inventor: John W. Shell, Los Altos, Calif.

[73] Assignee: Alza Corporation, Palo Alto, Calif.

[21] Appl. No.: 850,275

[22] Filed: Nov. 10, 1977

Related U.S. Application Data

[60] Continuation-in-part of Ser. No. 715,519, Aug. 18, 1976, abandoned, which is a division of Ser. No. 592,555, Jul. 2, 1975, Pat. No. 4,001,388, which is a continuation-in-part of Ser. No. 369,916, Jun. 14, 1973, Pat. No. 3,914,402.

[51] Int. Cl.$^2$ .......................... A61K 9/14; A61K 9/22; A61K 9/32
[52] U.S. Cl. ...................................... 424/14; 128/260; 424/16; 424/19; 424/20; 424/22; 424/31; 424/32; 424/78
[58] Field of Search ...................... 424/14, 16, 19-22, 424/31-33, 78; 128/260

[56] References Cited

U.S. PATENT DOCUMENTS

| | | | |
|---|---|---|---|
| 2,671,750 | 3/1954 | Macek | 424/243 |
| 2,828,319 | 3/1958 | Magerlein et al. | 424/243 X |
| 2,861,920 | 11/1958 | Dale et al. | 424/80 |
| 2,897,120 | 7/1959 | Cronin et al. | 424/80 |
| 3,062,712 | 11/1962 | Dale et al. | 424/80 |
| 3,755,558 | 8/1973 | Scribner | 424/47 |
| 3,773,919 | 11/1973 | Boswell et al. | 424/19 |
| 3,826,258 | 7/1974 | Abraham | 128/260 |
| 3,867,519 | 2/1975 | Michaels | 424/19 |
| 3,887,699 | 6/1975 | Yolles | 424/19 |
| 3,914,402 | 10/1975 | Shell | 424/32 |
| 4,001,388 | 1/1977 | Shell | 424/14 |

FOREIGN PATENT DOCUMENTS 2,602,994  7/1976  Fed. Rep. of Germany.

OTHER PUBLICATIONS

Chem. Abstracts, vol. 85: 144014k (1976), Abstr. of Ger. Offen. 2,602,994, Jul. 29, 1976, "Ortho Ester Polymers", Chol, Nam Sok; Heller, Jorge (Alza Corp), (U.S. 544808, Jan. 28, 1975).

*Primary Examiner*—Shep K. Rose
*Attorney, Agent, or Firm*—Paul L. Sabatine; Thomas E. Ciotti; Edward L. Mandell

[57] ABSTRACT

An ophthalmological bioerodible dosage form for ophthalmic drugs is disclosed. The dosage form comprises particles of 10 to 300 microns made of drug dispersed within a drug release rate controlling material which bioerodes in the environment of the eye.

4 Claims, 5 Drawing Figures

200 MICRONS

200 MICRONS

200 MICRONS

OCULAR SYSTEM MADE OF BIOERODIBLE ESTERS HAVING LINEAR ETHER

CROSS-REFERENCE TO RELATED APPLICATION

This application is a continuation-in-part of U.S. Pat. application Ser. No. 715,519 filed on Aug. 18, 1976, now abandoned which application is a division of Ser. No. 592,555 filed on July 2, 1975 and now U.S. Pat. No. 4,001,388 issued on Jan. 4, 1977, which patent is a continuation-in-part of U.S. Pat. application Ser. No. 369,916 filed on June 14, 1973, now U.S. Pat. No. 3,914,402 issued on Oct. 21, 1975. This application is assigned to the same assigned of the earlier filed applications and benefit of their filing dates is claimed.

BACKGROUND OF THE INVENTION

1. Field of the Invention

This invention relates to an improved dosage form for opthalmic drugs. More particularly, it relates to a new ocular dosage form which is easy to use and which achieves a controlled release of drug to the eye over a prolonged period of time.

2. The Prior Art

Most ocular treatments call for the administration of medicaments topically to the tissues of the ocular cavity. These medicaments have, in the prior art, assumed a wide range of forms. The most common dosage form for opthalmic medicaments is liquid drops. Liquid drops may be found for example, in over-the-counter ocular decongestants and in anti-glaucoma solutions, such as ½%, 1% or 2% aqueous solutions of pilocarpine salts. The liquid drop dosage form is easy to use, but suffers from the inherent disadvantage that the medication it contains is rapidly washed from the ocular cavity by tear flow. Thus, for drops, a continuous sustained level of medication is not achieved. Attempts to achieve sustained levels include periodic application of drops, but this results in the eye receiving a massive and unpredictable amount of medication. The result of this administration and washing is that the level of medication surges to a peak at the time the drops are applied, then the drug concentration falls rapidly. A plot of medication concentration in the eye versus time has the appearance of a series of peaks of drug level which may surpass the toxic threshold of the drug separated by extended valleys of drug level below the critical level needed to achieve the desired therapeutic effect.

Suspensions of particles of drug in liquids have been widely used as well; for example, hydrocortisone acetate and prednisolone acetate are typical of drugs presently marketed as suspensions. These suspensions usually contain preservatives, isotonicity adjusters, and suspending and dispersing agents. Present day suspensions create a variety of problems. First, they generally may only be made with relatively water-insoluble drugs, since soluble drugs form saturated solutions which have higher tonicities than the eye can easily adapt to. Also, the rate of release from the particles of the suspension is related to the rate of solubility of the drug so that one dosage rate alone may be obtained with a given drug. In the majority of cases, this one rate of delivery is not ideal.

Other dosage forms have been proposed, most on the basis that seemingly they give a more prolonged release of drug to the eye. These dosage forms include ointments, lamellae of glycerinated gelatin, such as described in U.S. Pat. No. 273,410 issued Mar. 6, 1883, and other similar dosage forms. These dosage forms give an only marginally more sustained drug release than do liquid drops, and most particularly, do not give a constant release pattern; additionally, they suffer the disadvantages of being difficult to sterilize and apply, and often cause blurring of vision.

Recently developed opthalmic drug delivery systems, such as described in U.S. Pat. No. 3,416,530 issued Dec. 17, 1968 and in U.S. Pat. No. 3,618,604 issued Nov. 9, 1971, do give true controlled deliveries of drug. The opthalmic drug delivery systems of these patents are unitary ocular inserts, several millimeters in size which are placed in the upper or lower sac of the eye to delivery a complete ophthalmic dosage regimen for a period of 24 hours or longer. While these ocular inserts do deliver drug to the eye continuously, and in a controlled manner, there remains improvements to be made. Many patients, especially the farsighted elderly, have difficulty inserting or removing ocular inserts. Also, the large unitary ocular inserts are at times accidentally ejected from the ocular cavity by the blinking action of the eyelids.

In view of the above presentation, it becomes immediately apparent that it would indeed be desirable to provide an opthalmic dosage form which makes available to the art the ease of administration of liquid drops combined with the drug releease characteristics of ocular inserts to improve the administration of ocular drugs.

STATEMENT OF THE INVENTION

In accordance with the present invention, a new ophthalmic dosage form is provided which combines the ease of administration of liquid drops with the improved drug release characteristics of drug releasing ocular inserts.

In one embodiment, the dosage form for ophthalmic drugs comprises solid particles that can be suspended in a liquid medium at a time prior to use, said particles comprising ophthalmic drug dispersed throughout a bioerodible drug release rate controlling material. These particles are from 10 to 300 microns in largest dimension.

In another embodiment, the particles each comprise an imperforate body of drug-impermeable bioerodible release rate-controlling material containing a drug dispersed throughout, which material bioerodes at a controlled rate over a prolonged period of time in response to the environment of the eye, thereby releasing the dispersed drug at a controlled rate over a prolonged period of time.

In yet another embodiment, the particles each comprise single depots of drug microencapsulated by an imperforate drug-impermeable bioerodible drug release rate-controlling material which material bioerodes at a controlled rate over a prolonged period of time in response to the environment of the eye, thereby releasing the microencapsulated drug by a process of controlled erosion at a controlled rate over a prolonged period of time.

In still yet other embodiments, the particles comprise either a solid drug-containing body or microcapsule made of a bioerodible material through which the drug is permeable at a controlled rate for a prolonged period of time.

In another embodiment, the dosage form comprises particles in emulsion form that are suspended in an ophthalmically-acceptable carrier for dispensing the particles to the eye with bioerosion of the particles occuring over time.

Although the solid particles are small enough to be passed from the ocular cavity through the punctum, this does not in fact happen. Instead, the particles when in suspension, painlessly dispersed and lodge in the soft tissues which line the surfaces of the palpebral and bulbar conjunctiva.

BRIEF DESCRIPTION OF THE DRAWINGS

In the drawings, which are not drawn to scale, but rather are set forth to illustrate various embodiments of the invention, the figures are as follows.

DETAILED DESCRIPTION OF THE INVENTION

Figure 1:
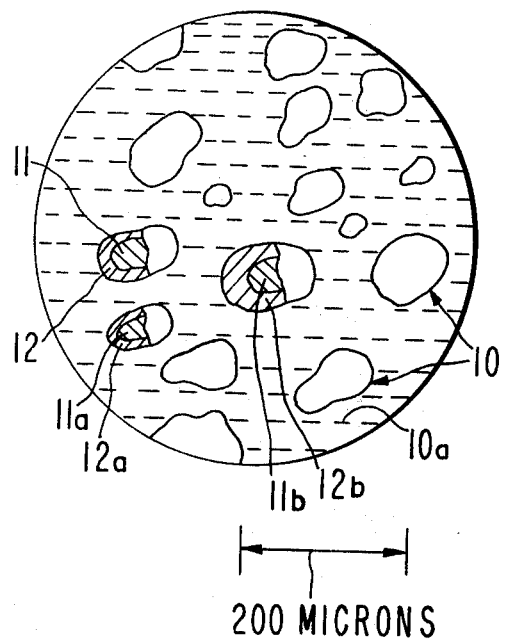
FIG. 1 is a magnified view of ophthalmic particles in accord with this invention, showing in partial cross-sectional view, one type of useful particle suspended in a liquid.

In its simplest form, the present dosage form includes a substantial plurality of 10 to 300 micron-sized particles containing drug and a drug release rate-controlling substance. The particles structurally can consist of an imperforate solid or an emulsified particle formed of the rate controlling substance. The liquid medium employed as a carrier for the particles is in a presently preferred use, added to the particles before they are administered to the eye, and the liquid medium used in the present suspension dosage form may be an aqueous or non-aqueous ophthalmically acceptable sterile liquid. Suitable non-aqueous liquid media include the physiologically acceptable oils such as silicone oil, USP mineral oil, white oil, and vegetable oils, for example corn oil, peanut oil, or the like. Aqueous media include water and physiological saline, which is generally preferred.

The dosage form optionally may contain other materials that are used to adjust pH, render the medium isotonic, preserve the dosage form and the like. Typical preservatives include benzalkonium chloride in a concentration of from 1:15,000 to 1:30,000, chlorobutanol in a concentration of from 0.3% to 0.8%, thimerosol in a concentration of from 0.001% to 0.003%, and phenyl mercuric nitrate in a concentration range of from 1:60,000 to 1:80,000. Agents may be added to increase viscosity, promote suspension and/or improve ocular compatibility, such as methyl cellulose in an amount of from 0.1% to 0.7% or poly(vinyl alcohol) in an amount of from 0.4% to 2%. These and other additive materials, are known in the art and are generally described in the book Contact Lens Practice by Robert B. Mandell, published by Charles C. Thomas, 1965 at pages 159 to 165, which description is incorporated herein by reference.

The particles, when suspended in the liquid medium, contain drug dispersed in a bioerodible drug release rate-controlled material. As used herein, a "drug release rate-controlling material" is defined to be a material which forms a particle containing physiologically active drug and prevents the drug from exhibiting instantaneously its physiological activity or regulates the rate at which the drug may be dispensed into the ocular environment. Only when the drug release rate-controlling material is eroded or when the drug diffuses through the rate controlling material may the drug be released. As used herein, the term "drug release rate-controlling material" is intended to include only those materials which truly function for the controlled release of drug over time. Fillers, binders and the like, are not included within these materials. The particle size also is important to the practice of the invention. If the particles are to painlessly lodge in the ocular tissues and to deliver drugs at a controlled rate, they must be of a size from 10 to 300 microns in largest dimension, preferably from 20 to 200 microns in largest dimension. The particles should also be sized such that a substantial plurality of particles, such as 100 or more, are delivered with each administration, to ensure a uniform delivery.

The drug release rate-controlling material must be bioerodible, that is, it must innocuously disintegrate or break down from a unit structure or enclosure over a prolonged period of time in response to the environment of the eye by one or more physical or chemical degradative processes, for example, enzymatic action, hydrolysis, ion exchange, or dissolution by solubilization, emulsion formation, or micelle formation. Likewise, the term "bioerode" is defined as the method by which such disintegration takes place. Bioerosion of the release rate-controlling material serves two purposes; not only may it release enclosed drug at a controlled rate, but also it prevents a build-up of particles in the tissues of the ocular cavity. In the particles used to form the suspensions of this invention, there are employed bioerodible materials which are non-toxic and compatible with the drug used, and which are capable of forming films which wholly surround and enclose drug particles. Exemplary materials which can be employed are as follows:

EXAMPLE 1

The drug release rate-controlling materials used to form the particles include polyesters of the general formula:

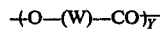

and mixtures thereof, wherein W is a lower alkylene of 1 to 7 carbons and in a presently preferred embodiment, include a member selected from the group of alkylenes of the formula

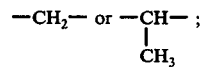

and Y has a value such that the molecular weight of the polymer is from about 4,000 to 100,000. The polymers are polymerization-condensation products of monobasic hydroxy acid of the formula $C_nH_{2n}(OH)COOH$ wherein n has a value of 1 to 7, preferably 1 or 2, and the acid is especially lactic acid or glycolic acid. Also included are copolymers derived from mixtures of these acids. The preparation of polymers of the formula I per se forms no part of the present invention. Several procedures are available and reported by Filachione, et al, Industrial and Engineering Chemistry, Vol. 36, No. 3, pages 223 to 228, March 1944, Tsuruta, et al, Macromol. Chem., Vol. 75, pages 211 to 214, 1964, and in U.S. Pat. Nos. 2,703,316; 2,668,162; 3,297,033; and 2,676,945. These polymers are hydrophobic and substantially impermeable to most drugs. Thus, they function best in particles which release encapsulated drug by an erosion mechanism. In a presently preferred embodiment, it is preferred to use a pharmaceutically acceptable liquid carrier in which the polyester is substantially insoluble but in which the polyester can erode at a controlled rate over a prolonged period of time while correspondingly releasing drug at a controlled and continuous rate over a prolonged period of time. Representative carriers suitable for forming the suspension of polyester particles include aqueous and saline carriers. The polyester in another embodiment is mixed with cellulose and cellulose derivatives such as cellulose ethers, methyl cellulose, ethyl cellulose and hydroxypropyl cellulose to enhance the acceptability of the product to the eye and produce particles that are bland and non-irritating to the eye.

EXAMPLE 2

Particles made of poly(peptide). An ophthalmically acceptable poly(peptide) is obtained by the selective hydrolysis of collagen, and comprises a complex mixture of high molecular weight water-soluble proteins. As used herein, the term "cross-linked poly(peptide)" means the degradative reaction product of a fibrous protein of animal origin that is prepared with a cross-linking agent which is reactive with either the hydroxyl, carboxyl or amino functional groups of the protein molecule but is substantially unreactive with the peptide linkages of the molecule. The product of cross-linking reaction preferably has an average molecular weight of from 20 to 50,000 between cross-links, while higher values can also be employed. These reaction products bioerode in the environment of the eye over a prolonged period of time. Cross-linked poly(peptide) materials and their preparations are well known. The degree of cross-linking is dependent upon the processing conditions employed and markedly affects the poly(peptide's) bioerodibility. Exemplary cross-linking agents are: aldehydes, such as monoaldehydes, e.g. $C_1$-$C_4$ aldehydes, dialdehydes, epoxides, para-benzene quinone, and aqueous peroxydisulfate. Aldehydes and ketones, especially the 1 to 4 carbon aldehydes and ketones are preferred, with formaldehyde being a most preferred cross-linking agent. Irradiation is another suitable method for cross-linking. See for example Y. Tomoda and M. Tsuda, J. Poly. Sci., Vol. 54, page 321, 1961. The preparation of poly(peptide) derived from collagen is described in The Encyclopedia of Chemistry, Edited by Clark and Hawley, pages 261 to 263, and 479 to 480, 1966, published by Reinhold Company.

The reactive hydroxyl, carboxyl and amino groups are respectively present in poly(peptide) in the appropriate amounts of 100, 75 and 50 meq per 100 grams. These quantities may serve as a general guide in detemining the amount of cross-linking agent to be used. Cross-linked poly(peptide) is relatively permeable to ocular fluid so that diffusion of drug through the polymer may take place to some extent. Thus, cross-linked poly(peptide) is a good example of a release rate-controlling material which releases drug by a diffusion mechanism.

EXAMPLE 3

The particles suitable for the purpose of the invention also can be made of poly(orthoesters). These have the following general formula:

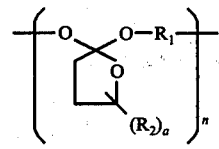

wherein $R_1$ is an alkylene of 4 to 12 carbons, a cycloalkylene of 5 to 6 carbons and an alkyleneoxy of 1 to 7 carbons, $R_2$ is a lower alkyl of 1 to 7 carbons, and a is 0 or 1. The polymers also include the cis, trans, the cis-/trans forms and the block and random copolymers. Exemplary of poly(orthoesters) include the polymers of the following formula wherein n is greater than 10:

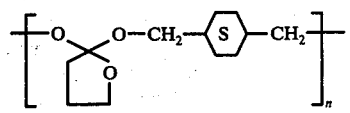

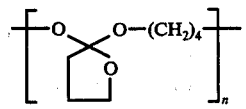

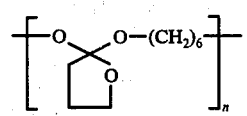

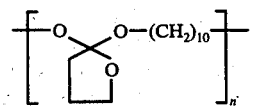

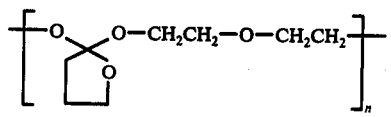

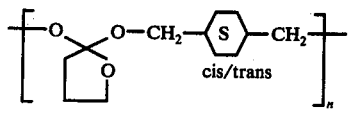

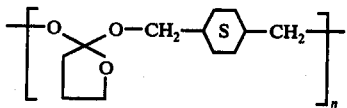

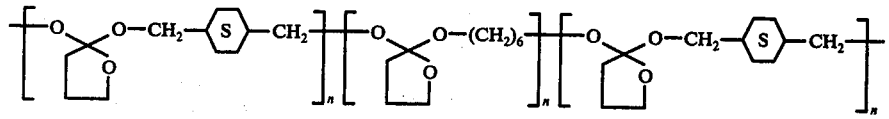

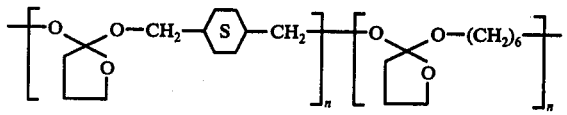

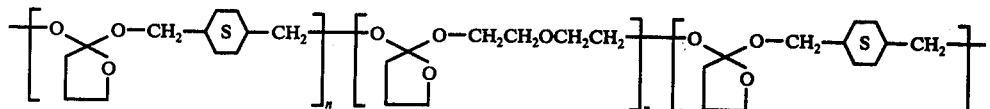

and

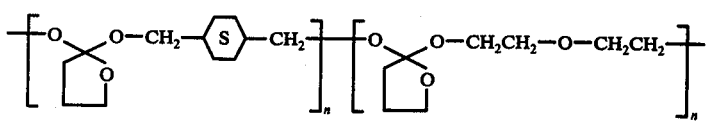

The poly(orthoester) particles bioerode in the environment of the eye at a controlled rate with a concomittant release of drug from the particle. The particles are prepared by heating the polymer and blending therein an ophthalmic drug. On cooling to room temperature, the polymers are conventionally processed to a particle size of 10 to 300 microns. The poly(orthoester) polymers are the invention of N. Choi and J. Heller as disclosed and claimed in copending U.S. Pat. application Ser. No. 544,808 filed on Jan. 28, 1975, which application is assigned to the same assignee as this application, and which application is herein incorporated by reference. Applicant uses the polymer of Ser. No. 544,808 for preparing the particles of the instant invention.

These materials are considered illustrative. Any bioerodible material which is compatible with the drug, non-toxic, non-irritating, and which has the desired erosion and diffusion release rate properties might also be used. The polyesters, cross-linked poly(peptides) and poly(orthoesters) set forth herein are presently preferred as release rate-controlling materials.

Ophthalmic drugs suitable for making the particles and the suspension, consistent with their known dosages and uses as disclosed in Remington's Pharmaceutical Sciences, 14th Edition, Parts VI to VIII, 1970, published by Mack Publishing Company, Easton, PA, and in The Pharmaceutical Basis of Therapeutics, by Goodman and Gilman, 4th Edition, 1970, published by MacMillan Co., London, are without limitation, solid opthalmic drugs including: antibiotics such as tetracycline, chlortetracycline, bacitracin, neomycin, polymyxin, gramicidin, oxytetracycline, chloramphenicol, gentamycin, penicillin, and erythromycin; antibacterials such as sulfonamides, sulfacetamide, sulfamethizole and sulfisoxazole; antivirals including idoxuridine; and other antibacterial agents such as nitrofurazone and sodium propionate; antiallergenics such as antazoline, methapyriline, chlorpheniramine, pyrilamine and prophenpyridamine; anti-inflammatories such as hydrocortisone, hydrocortisone acetate, dexamethasone, dexamethasone 21-phosphate, fluocinoline, medrysone, prednisolone, methylprednisolone, prednisolone 21-phosphate, prednisolone acetate, fluorometholone, betamethasone and triamcinolone; decongestants such as phenylephrine, naphazoline, and tetrahydrazoline; miotics and anticholinesterases such as pilocarpine, eserine salicylate, carbachol, di-isopropyl fluorophosphate, phospholine iodide, and demecarium bromide; mydriatics such as atropine sulfate, cyclopentolate, homatropine, scopolamine, tropicamide, eucatropine, and hydroxyamphetamine; and sympathomimetics such as epinephrine.

The solid drug and drug release rate-controlling material are combined in any fashion which enables small (10 to 300 micron) particles of dispersed drug to be formed which have the predominant portion of the drug fully dispersed throughout the rate controlling material.

DETAILED DESCRIPTION OF THE DRAWINGS

One suitable manner for combining drug and rate controlling material is illustrated in FIG. 1. FIG. 1 is a magnification of particles 10 in a liquid medium 10a to form an ophthalmic suspension. The particles are shown in an aqueous liquid; however, in a presently preferred embodiment, the particles are dry with the liquid added at the time of use. Particles 10, when sectioned, can be seen to comprise drug 11 within drug release rate-controlling material 12. As FIG. 1 illustrates, particles 10 are of variable size. It should be noted, the thickness of the release rate-controlling material varies; for example, compare 12 with 12a and 12b. This variation in the thickness of the erodible material or particle layers substantially prolongs the release of drug. Light coats will erode through rapidly, while heavier ones will take longer. By varying the relative proportions of various thicknesses, a variable release rate may be achieved. Also, by varying the nature of the coating material among a group of differently eroding materials, for example some rapid--some slow, a controlled prolonged release may be obtained. It can be seen that by adjusting the proportions of different coated particles, a constant rate of drug release can be obtained; that is, a release rate having a zero order dependence over time.

Any of the standard manufacturing techniques known in the art can be used to prepare particles 10. The drug can be added to the drug release rate-controlling material while it is in liquid or particle form, the mixture being reduced to fine particles by grinding, crushing, milling or the like. Alternatively, fine particles of the drug can be coated such as by suspending dry particles of the drug in an air stream and contacting that stream with a stream of rate controlling material that coats the drug with a solid wall of rate controlling material. The particles also can be manufactured by the process of co-ascervation. This process consists essentially of the formation of three immiscible phases consisting of a liquid manufacturing phase, a core material phase and a liquid coating phase. Liquid coating is deposited on the core material and rigidized usually by thermal, cross-linking or desolvation. Techniques for carrying out the process, such as the Bungenberg, de Jong and Kaas method, are reported in Biochem. Z., Vol. 323, 1931 pages 338 to b 345; and in J. Pharm. Sci., Vol. 59, No. 10, 1970, pages 1367 to 1367.

Figure 2:
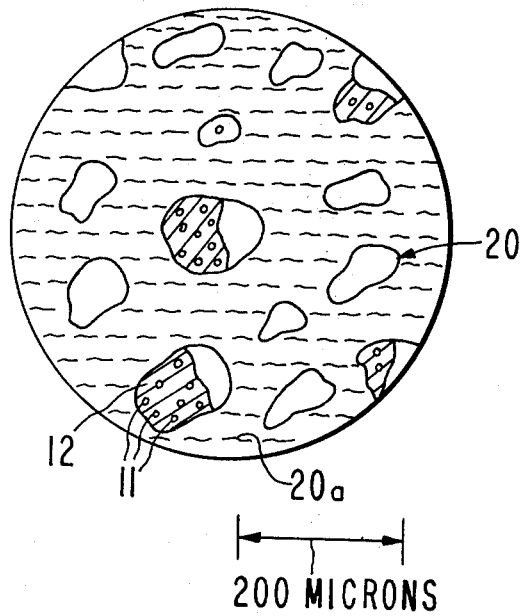
FIG. 2 is a view like FIG. 1 showing in partial cross-sectional view, another type of useful particle.

A second typical configuration which particles may assume is illustrated in FIG. 2. There, a variety of particles 20 are illustrated which each contain a number of depots of drug 11 dispersed through a body 12 of rate controlling material. The particles 20 are shown in an ophthalmically acceptable oil carrier 20a. Carrier 20a can be added when particles 20 are made or in a presently preferred embodiment, particles 20 are added to carrier 20a immediately prior to use. As the rate controlling material erodes, it gradually exposes and releases the drug from the particle 20. These type of particles could be easily formed by admixing 0.5 to 5 micron-sized drug particles and release rate-controlling material in a fluid phase and casting and settling a solid peice of drug and rate controlling material. This piece could then be micronized, such as in a commercially available CRC Micromill, to give the desired 10 to 300 micron particles of rate controlling material containing drug.

Figure 3:
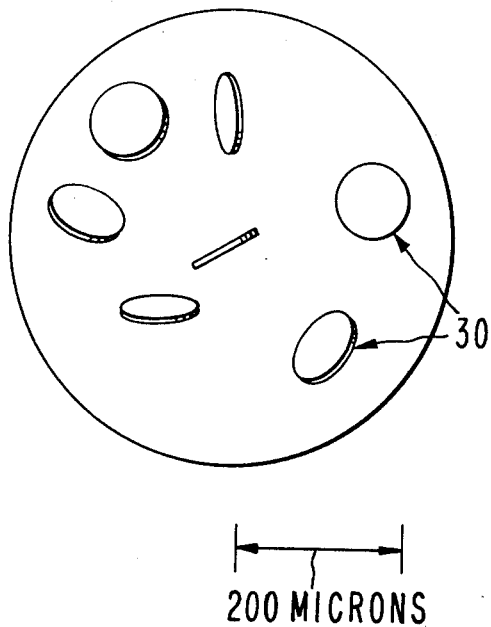
FIG. 3 is a view like FIG. 1 showing in perspective view, yet another type of useful particle.

FIG. 3 illustrates another embodiment of the invention which can yield a more constant rate of release. The particles of FIG. 3 are all substantially flat discs 30 essentially having only two dimensions. That is, one of each disc's dimensions is less than 10% of either of its other dimension. While round discs are shown in FIG. 3, clearly other two dimensional shapes could also be used. These two dimensional particles present an essentially constant surface area throughout their period of bioerosion. The particles internally are similar to particles 20 of FIG. 2; that is, they contain a plurality of drug depots dispersed through a body of release rate-controlling material. Also, disc 30 can be manufactured with drug homogeneously or heterogeneously dispersed throughout an erodible drug release rate material. Another way to obtain a constant rate of drug release with an ophthalmic suspension in accord with this invention, is to employ particles of the type shown in FIG. 1 (particles 10) having accurately controlled proportions of rate controlling wall material. By providing an accurately graded range of thickness of rate controlling material, a smooth flow of drug can be achieved.

The dosage forms of this invention, when in suspension, permit a uniform rate of ophthalmic drug delivery. Also, by their ability to prolong drug release, they permit the time periods between drop instillation to be greatly prolonged, such as to well over 4 hours, for example up to to 4 or 5 days, or even a week. Preferably, suspensions are used to prolong drug release over periods of from 18 to 72 hours per instillation. The suspension must therefore contain enough drug to satisfy the dosage requirements for these prolonged periods. It is generally preferred to adjust the amount of drug in the suspensions so that from about 2 to 10 drops of suspension contains the require complete dosage regimen.

Typical dosages for drugs administered in the improved dosage form are:

| | |
|---|---|
| Antibiotics, such as polymixin: | 250 micrograms/day |
| Sulfonamides, such as sulfacetamide: | 500 micrograms/day |
| Antivirals, such as idoxuridine: | 5 micrograms/day |
| Anti-inflammatories, such as hydrocortisone acetate or prednisolone: | 500 micrograms/day |
| Pilocarpine: | 25-500 micrograms/day |

The proportion of drug and drug release rate-controlling material can range from about 0.01 up to about 20 parts drug to 1 part rate controlling material to about 1 part drug to about 0.01 up to about 30 parts rate controlling material. The particles shall contain sufficient drug for the entire dosage regimen. The proportion of drug-containing particles to liquid medium of the suspension can range from about 1 part particles to 100 parts liquid to about 1 part particles to about 2 parts liquid. In summary, the suspensions of this invention generally contain the following proportions of components:

| | |
|---|---|
| Liquid medium | 100 parts |
| Particles | 1-50 parts |
| Drug | 0.3-45 parts |
| Rate-controlling material | 0.1-33 parts |
| Preservatives and the | |

| -continued | |
|---|---|
| like | (as required) |

When an aqueous medium is employed as the carrier to form the suspension, it is often desirable to take precautions to prevent undue erosion of the particles in the medium when the particles are suspended, especially at a time prior to use. This may be done chemically, for example by saturating the medium with dissolved drug release rate-controlling material in cases where bioerosion proceeds through solubilization, or by adjusting the solution pH, in cases where the rate controlling materials's erosion is pH dependent, to non-erodible ranges. It may also be done physically by separating the solid particles from the liquid medium until immediately prior to application. In a most elementary fashion, this may be carried out by adding a few drops of liquid to the particles prior to use.

Figure 4:
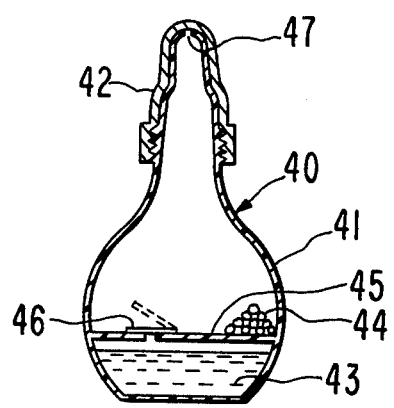
FIG. 4 is a cross-sectional view of an open container for mixing and administering the suspensions of this invention.
Figure 4A:
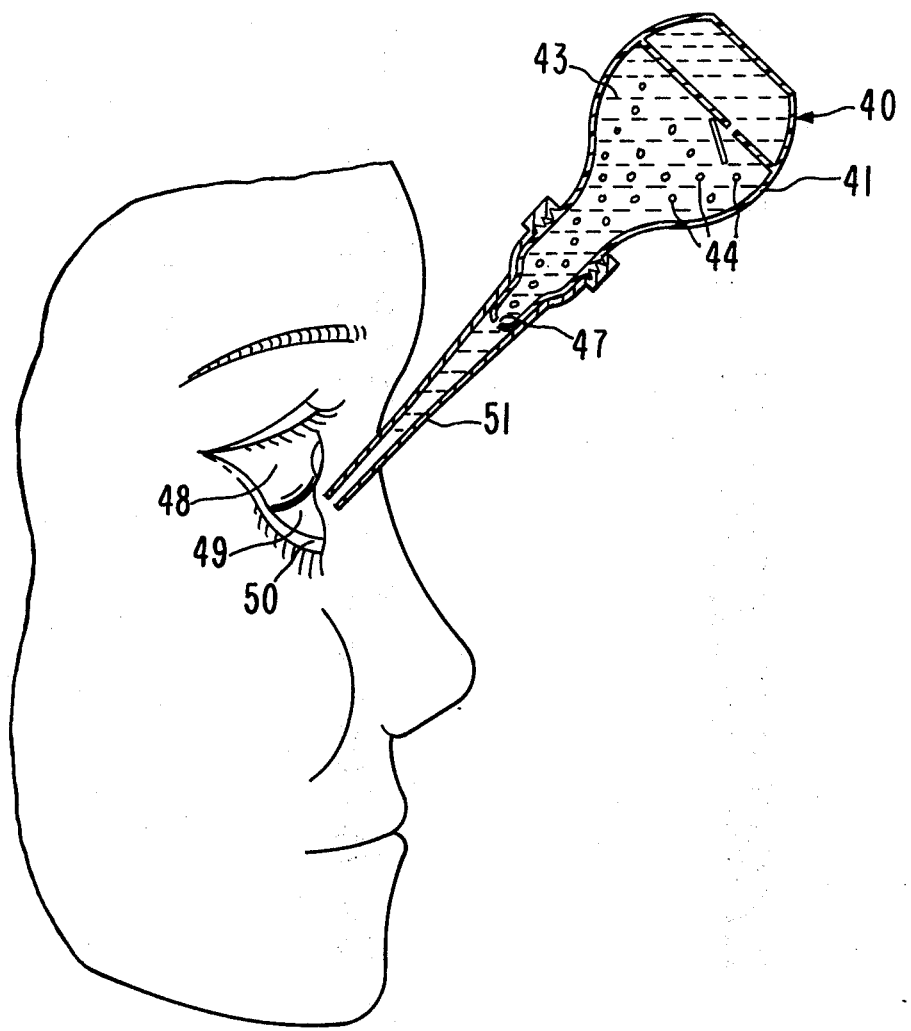
FIG. 4a is a cross-sectional view like FIG. 4, showing the container with a dropper attached thereto releasing medicine into the eye.

In FIG. 4, and FIG. 4a, a more accurate, more controlled addition of liquid can be carried out using a multi-chambered drug container such as shown in cross sectional form in FIG. 4 and FIG. 4a as container 40. Container 20 grossly seen is in the form of a single dosage dropper bottle of the type often used for ophthalmic preparations. It has an outer wall 41, generally of flexible plastic. Container 40 can also be made of glass. The top of wall 41 terminates in a small dropper tip having a hole 47. It may be a part of wall 41, as shown, or it may be a second separate insert plug. The latter configuration facilitates filling the container. The tip is equipped with a cover 42 to keep dirt, germs, and the like out and maintain sterility of the contents of container 40. Container 40 contains a measured amount of 20 to 200 micron-enclosed solid drug particles 44 in a second upper chamber. The two chambers are separated from one another by a barrier 45 carrying a valve 46. By squeezing the lower portion of device 40, the liquid 43 there contained is forced upward through the valve into the upper chamber and mixed with particles 44. A variation of this configuration could employ a rupture disc between the two chambers. The resulting suspension would have an accurately determined composition and would be easily administered to a patient's eye 48 as seen in FIG. 4a, via a dropper tip 51 that is suitably affixed to container 40 at the time of use. The ophthalmic formulation comprising particles 44 in carrier 43 are administered to conjunctival sac 49 as lower eyelid 50 is moved downward from eye 48. Thus, the invention provides a complete ophthalmic dosage form and a means for administering same.

PREPARATION OF OPHTHALMIC FORMULATIONS

EXAMPLE A 500 grams of chloramphenicol of a particle size of from 20 to 40 microns, is encapsulated with polylactic acid polymer of molecular weight 50,000, according to the following procedure: 250 grams of the polylactic acid is dissolved in 2 liters of chloroform. The chloramphenicol particles are coated with the polylactic acid using a Wurster air suspension technique. The coat thickness is determined to vary from 8 to 60 microns thick.

3 grams of the chloramphenicol microcapsules are dispersed in 50 cc's of an aqueous medium containing preservatives and salts to achieve ocular isotonicity. When drops of this dispersion are placed in the eye, the polylactic acid-coated particles imbed in the soft tissues lining the eyelids. They gradually release their chloramphenicol over a prolonged (48 hour) period. After about 96 hours, no residual polylactic acid is noted in the ocular cavity.

EXAMPLE B

The procedures of Example A are repeated, substituting 250 grams of crystalline pilocarpine nitrate for the chloramphenicol. The pilocarpine has an average particle size of 15 to 30 microns. The polylactic acid coating has a thickness ranging from 10 to 50 microns. When 3–4 drops of the resulting liquid suspension are added each day for a week to a patient's ocular cavities, it is noted that the patient's ocular pressures are continuously reduced from their normal levels, indicative of a prolonged controlled release of pilocarpine. This release pattern is especially effective as it avoids periods where no drug is being delivered.

EXAMPLE C

A suspension of cross-linked poly(peptide) particles containing hydrocortisone acetate for the treatment of eye inflammation is prepared as follows: a phosphate buffer is prepared from 1 liter of distilled water, 7.1 grams of disodium hydrogen phosphate and 6.9 grams of sodium dihydrogen phosphate monohydrate. The pH is 6.8. 40 Ml of the phosphate buffer and 0.15 grams chlorobutanol is combined with heating and stirring. 9 grams of poly(peptide) (Alantic Pharmagel 250 Bloom Type A USP) is added slowly with stirring to the 40 grams of buffer solution at 90° C. Alternatively, the poly(peptide) can be added to the buffer solution after it is cooled to room temperature, and the mixture then heated to 90° C until solution is complete.

3.1 grams of micronized (10 micron) hydrocortisone and 10 microliters of Tween 80 (Atlas, USP grade) are ground together and suspended in 5 ml of phosphate buffer. The resultant mixture is added immediately to the stirred poly(peptide) solution as it cools to approximately 50° C. The final mixture is stirred thoroughly for four minutes until the temperature falls to 40° C and poured onto a sheet of polyvinyl chloride. The resulting film is dried at room temperature for one day.

A solution of formaldehyde (1% by weight) is prepared by addition of 13.1 grams of 38% formaldehyde reagent to 487 grams phosphate buffer (pH 6.8). The poly(peptide) films are submerged in this buffered formaldehyde solution for 20 minutes at room temperature, quickly rinsed with water and soaked in ice water for 2 hours. The films are removed from the ice water and dried overnight. The dried film is then micronized to a particle size of about 100 microns.

A liquid medium consisting of sterile distilled water, 1% w. poly(vinyl alcohol) and 0.004% benzalkonium chloride is prepared. A suspension of about 2 parts particles in 100 parts liquid medium is prepared. When drops of this suspension are administered to the eye, the particles lodge in the linings of the ocular cavity. Ocular fluid permeates the poly(peptide) of the particles and drug diffuses out through the ocular fluid at a controlled rate over a prolonged period of time. The poly(peptide) erodes as well in the ocular environment.

EXAMPLE D

Particles of the preferred size containing hydrocortisone are prepared by heating 7.125 grams of the poly- (orthoester) of the following formula wherein the polymer had a cis/trans configuration:

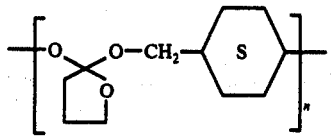

with 0.375 grams of hydrocortisone and mixing the polymer and the steroid to obtain a homogeneous mixture. After cooling to room temperature, the formulation is milled to the preferred micron size.

EXAMPLE E–F

The procedure of Example D is repeated in this example, with all the formulation procedures as described, except pilocarpine salt is used as the drug in one embodiment, and eserine salicylate is used as the drug in a separate particle formulation.

EXAMPLE G

Ophthalmic particles containing tetracycline are prepared by blending 4.750 grams of:

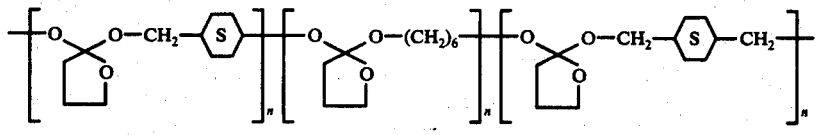

with 0.250 grams of tetracycline and milling the blend to the desired micron size.

While certain specific considerations have been disclosed and discussed herein, such have been offered solely to exemplify the present invention, and should in no way be considered as limiting the scope and nature of the invention.

I claim:

1. An ophthalmic dosage form comprising solid particles of from 0.01 up to 20 parts of an ophthalmic drug admixed with from 0.01 up to 30 parts of a bioerodible drug release rate-controlling orthoester homopolymer of the general formula:

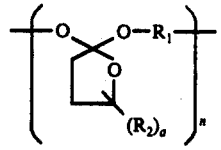

wherein $R_1$ is a member selected from the group consisting of alkylene of 4 to 12 carbons, a cycloalkylene of 5 to 6 carbons, and an alkyleneoxy of 1 to 7 carbons, $R_2$ is a lower alkyl of 1 to 7 carbons, a is 0 to 1, and n is greater than 10, said solid particles from 10 to 300 microns in largest dimensions, non-irritating and non-toxic to the eye, with from 1 to 5 parts of said solid particles admixed with a suspension agent and up to 100 parts of an ophthalmically-acceptable liquid medium having a pH acceptable to the eye, and when said liquid dosage form is dispensed to an eye, the solid particles bioerde in response to the environment of the eye at a controlled rate and administer drug over a prolonged period of time.

2. An ophthalmic dosage form according to claim 1, wherein the ophthalmic drug is a member selected from the group consisting of idoxuridine, pehnylephrine, pilocarpine, eserine, carbachol, phospholine iodine, demecarium bromide, cyclopentolate, homatropine, scopolamine and epinephrine.

3. An ophthalmic dosage form according to claim 1, wherein the drug is an ophthalmic steroid selected from the group consisting of hydrocortisone, hydrocortisone acetate, dexamethasone, dexamethasone prednisole 21-phosphate, prednisolone acetate, fluorometholone, beta-methasone and triamicinolone.

4. An ophthalmic dosage form according to claim 1, wherein the drug is an ophthalmic antibiotic selected from the group consisting of tetracycline, chlorotetracycline, bacitracin, neomycin, polymyxin, gramicidin, oxytetracycline, chloramphenicol, gentamycin, penicillin and erythromycin.

* * * * *